United States Patent
Suppes et al.

(10) Patent No.: US 9,146,327 B2
(45) Date of Patent: Sep. 29, 2015

(54) METHOD FOR DETERMINING GEOMETRIC IMAGING PROPERTIES OF A FLAT PANEL DETECTOR, CORRESPONDINGLY ADAPTED X-RAY INSPECTION SYSTEM AND CALIBRATION PHANTOM

(71) Applicant: GE Sensing & Inspection Technologies GmbH, Hurth (DE)

(72) Inventors: Alexander Suppes, Niedersachsen (DE); Pavel Pokutnev, Niedersachsen (DE); Eberhard Neuser, Lower Saxony (DE); Nils Rothe, Sachsen (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 46 days.

(21) Appl. No.: 14/082,641

(22) Filed: Nov. 18, 2013

(65) Prior Publication Data

US 2014/0153694 A1 Jun. 5, 2014

(30) Foreign Application Priority Data

Nov. 30, 2012 (EP) .................................... 12195054

(51) Int. Cl.
*G01N 23/04* (2006.01)
*G01T 7/00* (2006.01)
(Continued)

(52) U.S. Cl.
CPC ................ *G01T 7/005* (2013.01); *A61B 6/5258* (2013.01); *A61B 6/583* (2013.01); *A61B 6/585* (2013.01);
(Continued)

(58) Field of Classification Search
CPC ........ A61B 6/583; A61B 6/582; A61B 6/585; A61B 6/03; A61B 6/4233; A61B 6/587; G01T 7/005; G01N 23/04; G06T 11/005; G06T 5/006
USPC ........ 378/207, 20, 205, 62; 250/252.1, 269.1; 382/131, 154, 275
See application file for complete search history.

(56) References Cited

U.S. PATENT DOCUMENTS

| | | | |
|---|---|---|---|
| 4,233,507 A | * | 11/1980 | Volz ............................... 378/18 |
| 4,872,187 A | | 10/1989 | Nakahata et al. |

(Continued)

FOREIGN PATENT DOCUMENTS

| | | |
|---|---|---|
| DE | 19509007 A1 | 9/1996 |
| DE | 102005033187 A1 | 1/2007 |

(Continued)

OTHER PUBLICATIONS

International Search Report and Written Opinion issued in connection with corresponding PCT Application No. PCT/EP2013/075293 on Feb. 17, 2014.

(Continued)

*Primary Examiner* — David A Vanore
(74) *Attorney, Agent, or Firm* — GE Global Patent Operation; Douglas D. Zhang (57) ABSTRACT

A method and system for determining geometric imaging properties of a flat panel detector in an x-ray inspection system are described herein. The method can include arranging a calibration phantom between an x-ray source and the flat panel detector, the calibration phantom including at least one discrete geometric object. Additionally, the method can include recording at least one x-ray image of the calibration phantom with the flat panel detector. At least one discrete geometric shape is generated in the x-ray image by imaging the at least one discrete geometric object of the calibration phantom. Further, the method can include determining a location-dependent distortion error of the flat panel detector from the at least one x-ray image on the basis of at least one characteristic of the at least one discrete geometric shape. All characteristics of the at least one discrete geometric shape used for determining the location-dependent distortion error are independent of the dimensions of the calibration phantom.

15 Claims, 6 Drawing Sheets

(51) Int. Cl.
*A61B 6/03* (2006.01)
*A61B 6/00* (2006.01)

(52) U.S. Cl.
CPC .............. *G01N 23/046* (2013.01); *A61B 6/03* (2013.01); *A61B 6/4233* (2013.01); *G01N 2223/303* (2013.01); *G01N 2223/3035* (2013.01); *G01N 2223/419* (2013.01)

(56) References Cited

U.S. PATENT DOCUMENTS

| | | | | |
|---|---|---|---|---|
| 4,985,906 | A | * | 1/1991 | Arnold ........................ 378/18 |
| 5,442,674 | A | * | 8/1995 | Picard et al. ................. 378/20 |
| 5,493,601 | A | * | 2/1996 | Fivez et al. ................. 378/207 |
| 5,764,719 | A | | 6/1998 | Noettling |
| 5,841,835 | A | * | 11/1998 | Aufrichtig et al. .......... 378/207 |
| 6,148,057 | A | * | 11/2000 | Urchuk et al. ............... 378/18 |
| 6,302,582 | B1 | * | 10/2001 | Nord et al. ................. 378/207 |
| 7,113,631 | B2 | * | 9/2006 | Vaillant et al. ............. 382/154 |
| 7,548,640 | B2 | * | 6/2009 | Jeunehomme et al. ....... 382/132 |
| 8,517,608 | B1 | * | 8/2013 | Arnold ...................... 378/207 |
| 2003/0118227 | A1 | * | 6/2003 | Winsor et al. .............. 382/132 |
| 2005/0094771 | A1 | * | 5/2005 | Basu et al. ................. 378/207 |
| 2009/0268865 | A1 | * | 10/2009 | Ren et al. .................... 378/37 |
| 2011/0233394 | A1 | * | 9/2011 | Glasser et al. ............. 250/252.1 |
| 2012/0012742 | A1 | * | 1/2012 | Ren et al. ................. 250/252.1 |
| 2013/0089186 | A1 | * | 4/2013 | Payne et al. ................ 378/207 |
| 2014/0056495 | A1 | * | 2/2014 | Janssens ..................... 382/128 |
| 2014/0064458 | A1 | | 3/2014 | Jobst et al. |
| 2014/0112565 | A1 | * | 4/2014 | Roessl et al. ................ 382/131 |
| 2014/0153694 | A1 | * | 6/2014 | Suppes et al. ................ 378/62 |
| 2014/0211925 | A1 | * | 7/2014 | Dong et al. ................. 378/207 |
| 2014/0376701 | A1 | * | 12/2014 | Kopperdahl et al. ......... 378/207 |
| 2015/0001383 | A1 | * | 1/2015 | Inanc et al. ............... 250/252.1 |

FOREIGN PATENT DOCUMENTS

| | | |
|---|---|---|
| DE | 102010050949 A1 | 11/2010 |
| DE | 102011075527 A1 | 11/2012 |
| EP | 0021366 A1 | 1/1981 |
| EP | 0479618 A2 | 4/1992 |
| WO | 200000086 A1 | 1/2000 |
| WO | 2012062543 A1 | 5/2012 |

OTHER PUBLICATIONS

Kruth et al., "Computed tomography for dimensional metrology", CIRP Annals—Manufacturing Technology, vol. No. 60, Issue No. 2, pp. 821-842, 2011.

* cited by examiner

METHOD FOR DETERMINING GEOMETRIC IMAGING PROPERTIES OF A FLAT PANEL DETECTOR, CORRESPONDINGLY ADAPTED X-RAY INSPECTION SYSTEM AND CALIBRATION PHANTOM

BACKGROUND TO THE INVENTION

The present invention relates to a method for determining geometric imaging properties of a flat panel detector in an x-ray inspection system for non-destructive material testing, including the steps arranging a calibration phantom between an x-ray source and the flat panel detector, the calibration phantom comprising at least one discrete geometric object; recording at least one x-ray image of the calibration phantom with the flat panel detector, with at least one discrete geometric shape being recorded by imaging the at least one discrete geometric object of the calibration phantom; and determining a location-dependent distortion error of the flat panel detector from the at least one x-ray image on the basis of at least one characteristic of the at least one discrete geometric shape. An embodiment of the present invention further relates to a correspondingly adapted x-ray inspection system and a corresponding calibration phantom.

The testing accuracy of an x-ray inspection system for non-destructive material testing with a flat panel detector inter alia depends on the geometric model of the detector taken as the basis in reconstruction and evaluation matching the dimensions of the real detector as exactly as possible. Contrary to former assumptions it has turned out that flat panel detectors within the bounds of the desired high testing accuracies are not flat but show a bend or curvature of the detector surface. It is also possible that for example the pixel size of flat panel detectors is not constant but is a function of the location, i.e. depends on the line number and column number. Distortion errors are thus caused, i.e. the coordinate of the real image of a characteristic, for example of one point, compared to the ideal image is dislocated due to the curvature or the non-constant pixel size.

For the correction of distortion errors of a flat panel detector, document WO 2012 062543 A2 proposes a method for operating a measurement arrangement for a computer tomograph, with a calibration phantom being arranged between the radiation source and the flat panel detector, and at least one x-ray image of the calibration phantom being recorded with the flat panel detector, and a distortion error of the flat panel detector being determined from known dimensions of the calibration phantom and from the at least one x-ray image as a function of the location. The calibration phantom comprises a plurality of separate structures, for example spheres, the dimensions of which, i.e. size and distances, must be known exactly. This usually requires a high-precision measurement of the calibration phantom, for example by use of a coordinate measuring instrument, thus involving a lot of time and high costs.

SUMMARY OF THE INVENTION

Embodiments of the present invention include a x-ray inspection method, an x-ray inspection system and a calibration phantom, with simple means allowing an exact determination of geometric imaging properties of the flat panel detector, to enable a correction of a corresponding distortion error, and thus, to improve the measuring precision of the x-ray inspection system.

An embodiment of the present invention achieves this goal through the features of the independent claims. In an embodiment of the present it is not necessary to have dimensions of the calibration phantom for determining the location-dependent distortion error. In fact, characteristics of the at least one discrete geometric shape, which are independent of the dimensions of the calibration phantom, are sufficient for this purpose, without an adverse effect on the resulting calibration accuracy. Compared to conventional methods, an embodiment of the present invention provides an advantage of dispensing with a previously time-consuming, high-precision measurement of the calibration phantom, for example by use of a coordinate measuring instrument.

In an embodiment of the present invention, various characteristics of the at least one discrete geometric shape are suited for the determination of the location-dependent distortion error. In the following, different characteristics are explained in more detail.

In an embodiment, a plurality of discrete geometric shapes is recorded at different positions by imaging the at least one discrete geometric object of the calibration phantom. This can be done in particular by use of a calibration phantom comprising a plurality of discrete geometric objects which can be imaged simultaneously by the x-ray device. Alternatively, for example it is also possible that the calibration phantom comprises just one discrete geometric object which is imaged by the x-ray device at different positions, one by one, of the detector surface.

The geometric objects forming the basis of the geometric shapes can be uniform, with a characteristic taken as the basis for the determination of the location-dependent distortion error being the deviation of the geometric shapes from uniformity. For example, the geometric objects forming the basis of the geometric shapes can be of equal size, with a characteristic taken as the basis for the determination of the location-dependent distortion error being a deviating size among the geometric shapes. In this embodiment, it is only required that the geometric objects of the sample forming the basis of the geometric shapes are of equal size with high precision, however it is not necessary to have knowledge of the size itself. The geometric objects forming the basis of the geometric shapes, for example can also have an equal shape, with a characteristic taken as the basis for the determination of the location-dependent distortion error being the deviating shape among the geometric shapes. In an embodiment, the geometric objects forming the basis of the geometric shapes can be arranged at regular intervals and/or periodically, with a characteristic taken as the basis for the determination of the location-dependent distortion error being the arrangement of the geometric shapes deviating from regularity and/or periodicity.

It is not compulsory that a plurality of discrete geometric shapes is recorded at different positions of the detector surface. Embodiments in which just one discrete geometric shape covering a significant area of the detector surface is recorded are also possible.

In an embodiment, the geometric object forming the basis of the geometric shape can be at least one straight line or can be arranged in at least one straight line, with a characteristic taken as the basis for the determination of the location-dependent distortion error being the deviation of the geometric shape from straightness. In an embodiment of the present invention, the geometric object forming the basis of the geometric shape can be at least one cylindrical object having a constant diameter, with a characteristic taken as the basis for the determination of the location-dependent distortion error being a deviation of the geometric shape from the constant diameter.

The location-dependent distortion error is not determined from one or more two-dimensional radiographic images but from a three-dimensional x-ray image in particular reconstructed using computer tomography. In particular, in a computer tomography system, this provides the advantage that the present reconstruction algorithms can also be used for the calibration. Furthermore, a three-dimensional x-ray image in particular reconstructed using computer tomography allows a more exact determination of the location-dependent distortion error.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
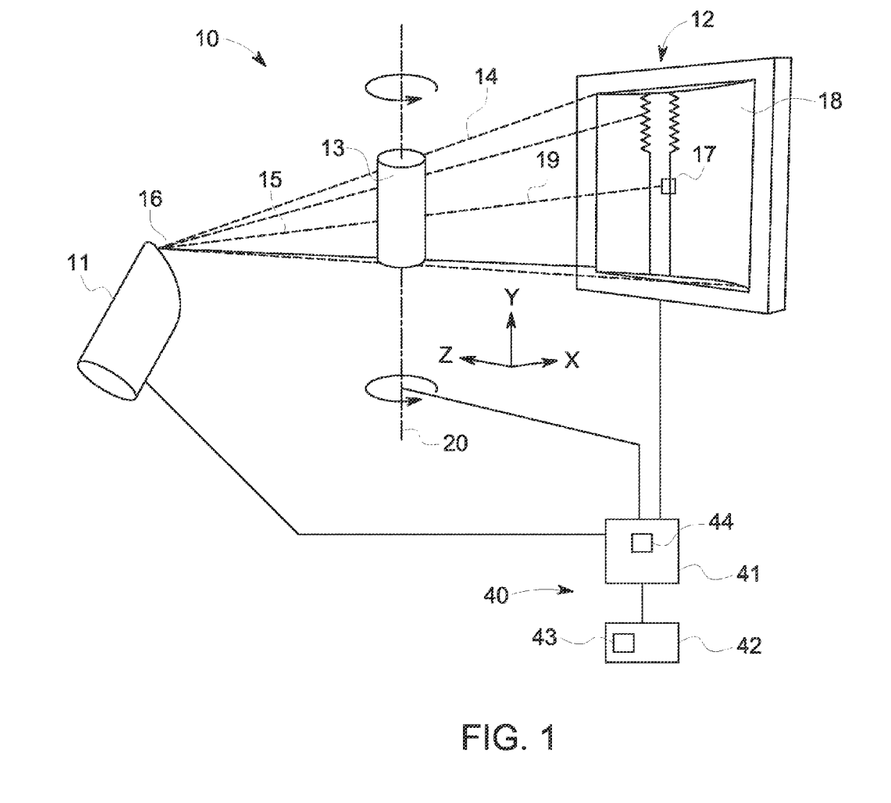
FIG. 1 a schematic illustration of a computer tomography system.

The computer tomography ("CT") system shown in FIG. 1 includes an x-ray device 10 for recording x-ray projections of a sample 13. For this purpose, the x-ray device 10 comprises an x-ray source 11, in particular an x-ray tube emitting an x-radiation cone 14, and an imaging x-ray detector 12. Furthermore, an only schematically sketched sample manipulator 20, which can be adapted to rotate the sample 13 around a vertical axis, is provided. In an embodiment, the x-ray device 10 can be rotated around the fixed sample 13. The sample 13 can be displaced by the sample manipulator 20 linearly in x-, y- and/or z-direction. In an embodiment, the x-ray device 10 and the sample 13 can appropriately be adjusted relatively to each other, in each case including rotation and/or translation around one or more axes.

The imaging x-ray detector 12 is a flat panel detector, in an embodiment a solid-state detector or semiconductor detector, which in an embodiment comprises a scintillation layer for transforming the incident x-radiation into light and a light-sensitive layer in particular formed by photo cells or photo diodes for transforming the light into an electric signal. In an embodiment, an x-radiation-sensitive photo conductor, for example on the basis of Selenium, is provided instead of a scintillation layer and a light-sensitive layer.

A set of x-ray projections of the sample 13 is recorded by the manipulator 20 being rotated by one small angular step at a time and one x-ray projection being recorded at each angular position. An x-ray projection 18, as for example shown in FIG. 1, is a two-dimensional image, with the detected density value of a pixel 17, typically a grey tone, indicating the attenuation of the corresponding x-ray beam 15 from the focal spot 16 of the x-ray source 11 through the sample 13, by which an attenuated x-ray beam 19 results in the corresponding pixel 17. Due to a curvature of the sensitive surface of the detector 12 it is possible that an object point is not imaged on the ideal pixel 17 but on another position or another pixel.

The recorded x-ray projections are read out from the x-ray detector 12 and are transmitted to a computer device 40, where they are stored in a storage device 44 for further evaluation and processing. The computer device 40 includes a programmable computer 41, in particular with a micro processor or a micro controller, and an operation terminal 42 with a display 43. The computer 41 includes a software for performing an appropriate ct reconstruction algorithm to determine a three-dimensional reconstructed image (volume image) of the sample 13 from the recorded x-ray projections. In an embodiment, a separate computer can be provided for carrying out the reconstruction. In an embodiment according to FIG. 1, the computer 41 is adapted to control the x-ray device 10, in particular the x-ray source 11, the x-ray detector 12 and the sample manipulator 20. In an embodiment, a separate control device can be provided for controlling the x-ray device 10.

For the calibration of the flat panel detector 12 a calibration phantom 13 is placed into the beam path 14 of the x-ray device 10, then x-ray images or x-ray projections of the calibration phantom 13 are recorded and the volume density of the calibration phantom 13 is reconstructed.

Figure 2:
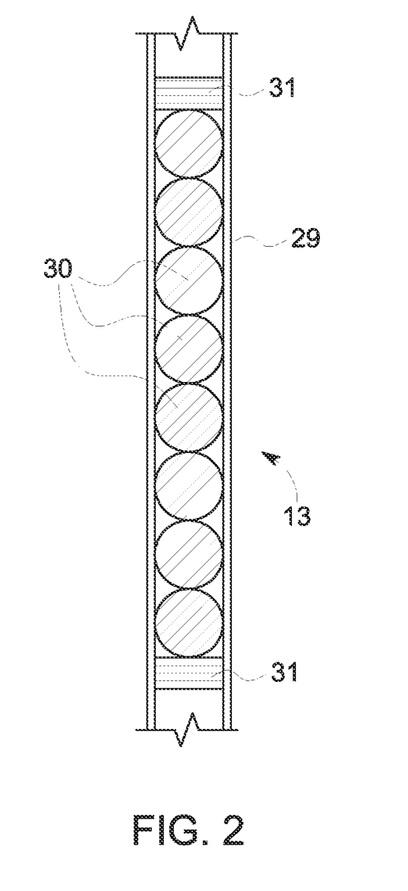
FIG. 2 a schematic longitudinal cut through a calibration phantom in an embodiment.

An embodiment of a calibration phantom 13 is shown in FIG. 2. In a tube 29 made of a suitable, particularly radiation-transparent material, in an embodiment a plastic material or aluminum, a single row of spheres 30 made of a suitable radiation-absorbing material, in an embodiment steel or ceramic, particularly is arranged in such a way that the spheres contact each other. The spheres 30 form a plurality of separate calibration objects not connected with each other. The inner diameter of the tube 29 is larger than the diameter of one sphere 30, however it is smaller than the double diameter of one sphere 30. The tube 29 can be closed at both ends via elastic closing objects 31, for example made of a foam material clamping and thus fixing the spheres 30 in the tube 29 to prevent the spheres 30 from shaking. With a desired high precision, for example in the range of ±1 μm, the spheres 30 have equal dimensions, i.e. an equal diameter, which does not have to be known with the same precision for carrying out the calibration process, and usually is just known with a significantly higher tolerance. For example, the diameter of the spheres 30 can be in a manufacturing tolerance range of ±100 μm (or more) about a nominal value, provided that the diameter variation among the spheres 30 is small (for example in the range of ±1 μm). For example, it is possible to use comparatively cost-effective ball bearing spheres as calibration objects 30. The diameter of ball bearing spheres indeed can vary significantly from one lot to the other, however ball bearing spheres within one lot usually with a very high precision have an equal diameter which however is not known exactly. For this reason, for example ball bearing spheres of the same lot can simply be used as calibration objects 30 for the present calibration process; a high-precision measurement of the diameter of the spheres 30 is not necessary.

The calibration phantom 13 is arranged along or parallel to the rotational axis (vertical axis or y-axis in FIG. 1), so that the spheres 30 are distributed over the extension (here the height) of the detector 12, and then x-ray projections are recorded. An x-ray image or an x-ray projection of the calibration phantom 13 from FIG. 2 is shown for example in FIG. 3. The row of spheres 30 of the calibration phantom 13 results in a corresponding row of sphere shapes 32 in the x-ray image. In the computer 41, a volume image of the calibration phantom 13 with three-dimensional sphere shapes 32 is reconstructed from all projections. The diameter of the three-dimensional sphere shapes 32 is determined from the reconstructed volume image in the computer 41 via evaluation or image processing. The relative diameter variation 33 of the three-dimensional sphere shapes 32 for example is plotted in FIG. 4 over the sphere row (here ten measurements corresponding to ten spheres 30). An embodiment illustrated by FIG. 4 shows the relative diameter deviation 33, for example in mm over the detector extension (here height) for example in pixel. As the diameter deviation or the diameter variation is not constant, conclusions with respect to the detector curvature can be drawn after an allocation to the corresponding detector positions.

Comparable measurements are carried out over the whole or a large part of the sensitive surface of the detector 12 by the calibration phantom 13 successively being displaced perpendicular to its longitudinal extension and corresponding x-ray images being recorded. If the calibration phantom 13 for example is arranged parallel to the rotational axis, the displacement is expediently carried out perpendicular to the rotational axis. The resulting two-dimensional diameter deviation 34 for example in mm over the detector height and detector width, each for example in pixel, said embodiment is an embodiment illustrated in FIG. 5. The two-dimensional curvature of the detector 12 can be determined accordingly. A location-dependent distortion error, i.e. a pixel-precise distortion error depending on the x- and y-coordinate of each pixel, can be determined from the curvature of the detector 12, and in particular can be stored in the computer 41. Each subsequently measured x-ray projection can then be corrected to the determined distortion error, by which the precision of the measured projections and thus also of the reconstructed data can be improved significantly. In an embodiment, the distortion error can be taken into account during the reconstruction, without the need to correct the x-ray projections themselves. In addition or as an alternative to the curvature of the sensitive detector surface, the pixel size or the local pixel size deviation can be determined in a pixel-precise manner.

Figure 6:
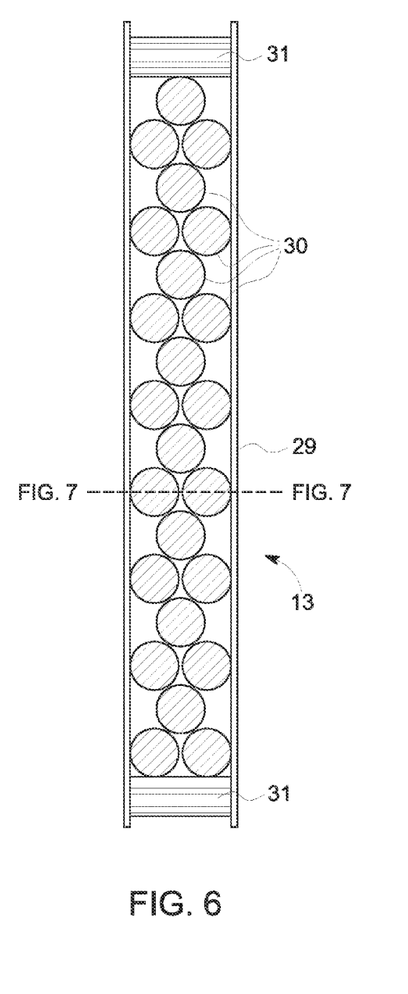
FIG. 6 a schematic longitudinal cut through a calibration phantom in a further embodiment.
Figure 7:
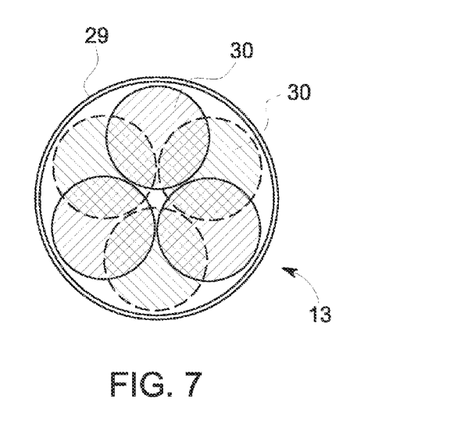
FIG. 7 a schematic cross-sectional cut through the calibration phantom from FIG. 6.

An embodiment of the calibration phantom 13 is shown in FIGS. 6 and 7. The inner diameter of the tube 29 is larger than the double, particularly larger than 2.1547 times the diameter of one sphere 30. In this way, a plurality of spheres 30, particularly at least three spheres 30, can be arranged in a plane perpendicular to the rotational axis. In the next sphere plane, the three-sphere group is turned by 60°, as is apparent from the cross-sectional cut according to FIG. 7. In this embodiment is that for each axial position several measured values are available allowing an averaging and thus an improvement in the measuring precision. Embodiments with two spheres or more than three spheres per plane perpendicular to the rotational axis are also possible.

Figure 9:
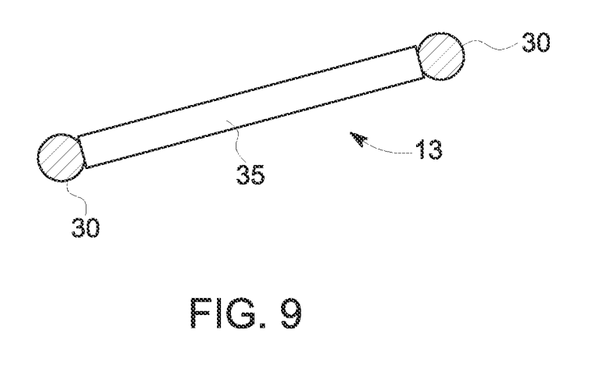
FIG. 9 a schematic illustration of a calibration phantom in an alternative embodiment.
Figure 10:
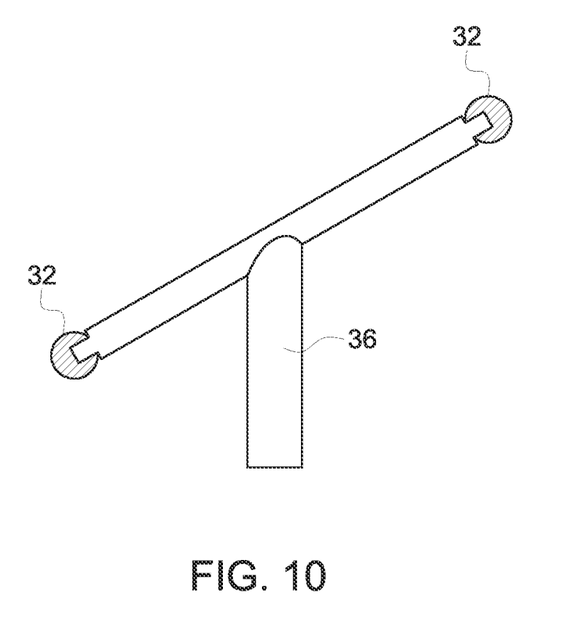
FIG. 10 a schematic reproduction of an x-ray image of a calibration phantom according to FIG. 9.

An embodiment of the calibration phantom 13 is shown in FIGS. 9 and 10. The rod-shaped calibration phantom 13 includes a radiation-transparent rod 35, for example made of CFRP, to each end of which one sphere-shaped radiation-absorbing calibration object 30 made of a suitable material, for example ruby, is fixed. The length of the rod does not have to be known and for example is in the range between 2 mm and 200 mm. The rod-shaped calibration phantom 13 can be recorded at different positions of the detector 12 and a curvature of the detector 12 can be derived from the relative deviations of the lengths with respect to each other. In a corresponding x-ray image shown in FIG. 10 a holder 36 not yet shown in FIG. 9 can be seen.

The application is not only applicable to computer tomography systems but also to non-CT x-ray inspection systems based on transmission. The application is particularly applicable to inspection systems for the non-destructive inspection of non-biological test objects.

The calibration phantom 13 is not limited to the shown embodiments. The calibration phantom, for example can be a plate-shaped calibration phantom 13 in the form of a mask with calibration objects, for example in the form of parallel or grid-like arranged lines, deviations of the lines from the straightness being determined in the x-ray image. The calibration objects, for example can also be equally spaced circles, crosses or the like, where, however, the exact distance does not have to be known. An embodiment is a cylinder, for example made of steel, having a high diameter constancy along the axis, deviations of the diameter along the cylinder axis being determined in the x-ray image. Various alternative embodiments of the calibration phantom 13 are possible.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural element with insubstantial differences from the literal languages of the claims.

What is claimed is:

1. A method for determining geometric imaging properties of a flat panel detector in an x-ray inspection system, the method comprising:
   arranging a calibration phantom between an x-ray source and the flat panel detector, wherein the calibration phantom comprises at least one discrete geometric object;
   recording at least one x-ray image of the calibration phantom with the flat panel detector, wherein at least one discrete geometric shape is generated in the x-ray image by imaging the at least one discrete geometric object of the calibration phantom; and
   determining a location-dependent distortion error of the flat panel detector from the at least one x-ray image on the basis of at least one characteristic of the at least one discrete geometric shape;
   wherein all of the at least one characteristic of the at least one discrete geometric shape used for determining the location-dependent distortion error are independent of the dimensions of the calibration phantom.

2. The method according to claim 1, wherein a plurality of discrete geometric shapes is recorded at different positions of the detector surface by imaging the at least one discrete geometric object of the calibration phantom.

3. The method according to claim 2, wherein the at least one discrete geometric object are uniform, and a characteristic of the at least one characteristic is the deviation of the geometric shapes from uniformity.

4. The method according to claim 2, wherein the at least one discrete geometric object are of equal size, and a characteristic of the at least one characteristic is a deviating size among the geometric shapes.

5. The method according to claim 2, wherein the at least one discrete geometric object have an equal shape, and a characteristic of the at least one characteristic is the deviating shape among the geometric shapes.

6. The method according to claim 2, wherein the at least on discrete geometric object are arranged at regular intervals and/or periodically, and a characteristic of the at least one characteristic is the arrangement of the geometric shapes deviating from regularity and/or periodicity.

7. The method according to claim 2, wherein the at least on discrete geometric object are arranged to contact each other.

8. The method according to claim 1, wherein the at least one discrete geometric object is at least one straight line or is arranged in at least one straight line, and a characteristic of the at least one characteristic is the deviation of the geometric shape from straightness.

9. The method according to claim 1, wherein the at least one discrete geometric object is at least one cylindrical object having a constant diameter, and a characteristic of the at least one characteristic is a deviation of the geometric shape from the constant diameter.

10. The method according to claim 1, wherein the at least one characteristic of the at least one geometric shape and/or the location-dependent distortion error is determined from a three-dimensional reconstructed x-ray image.

11. An X-ray inspection system comprising an x-ray source, a flat panel detector, a calibration phantom comprising at least one discrete geometric object, and an electronic data processing device, wherein the x-ray inspection system is adapted to record at least one x-ray image of the calibration phantom placed between the x-ray source and the flat panel detector, at least one discrete geometric shape is generated in the x-ray image by imaging the at least one discrete geometric object of the calibration phantom, the data processing device is adapted to determine a location-dependent distortion error of the flat panel detector from the at least one x-ray image on the basis of at least one characteristic of the discrete geometric shape, all of the at least one characteristics of the at least one discrete geometric shape used for determining the location-dependent distortion error are independent of the dimensions of the calibration phantom or of exactly knowing the dimensions of the calibration phantom.

12. A calibration phantom for determining geometric imaging properties of a flat panel detector in an x-ray inspection system, comprising a cylindrical tube and a row of uniform geometric objects arranged in the cylindrical tube, wherein the row of uniform geometric objects are not connected with each other and/or are arranged to contact each other.

13. The calibration phantom according to claim 12, wherein the row of uniform geometric objects are spheres having an equal diameter.

14. The calibration phantom according to claim 12, wherein a plurality of geometric objects, are arranged in a plane perpendicular to the tube axis.

15. The calibration phantom according to claim 12, wherein a plurality of geometric objects are arranged in a plane perpendicular to the tube axis, wherein the plurality of geometric objects comprise at least three geometric objects.

* * * * *

UNITED STATES PATENT AND TRADEMARK OFFICE
CERTIFICATE OF CORRECTION

| | | |
|---|---|---|
| PATENT NO. | : 9,146,327 B2 | Page 1 of 2 |
| APPLICATION NO. | : 14/082641 | |
| DATED | : September 29, 2015 | |
| INVENTOR(S) | : Suppes et al. | |

It is certified that error appears in the above-identified patent and that said Letters Patent is hereby corrected as shown below:

On the Title Page, in Item (71), under "Applicant", in Column 1, Line 2, delete "Hurth (DE)" and insert -- Hürth (DE) --, therefor.

On the Title Page, in Item (73), under "Assignee", in Column 1, Line 2, delete "Hurth (DE)" and insert -- Hürth (DE) --, therefor.

IN THE SPECIFICATION

In Column 1, Lines 42-43, delete "tomograph," and insert -- tomography, --, therefor.

In Column 3, Line 20, delete "FIG. 1 a" and insert -- FIG. 1 is a --, therefor.

In Column 3, Line 22, delete "FIG. 2 a" and insert -- FIG. 2 is a --, therefor.

Figure 3:
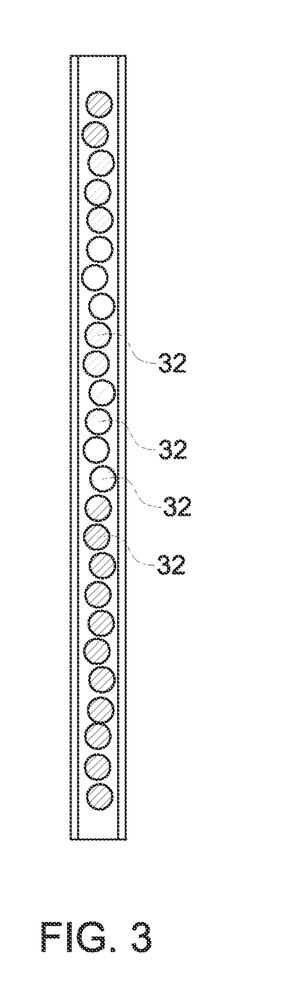
FIG. 3 a schematic reproduction of an x-ray image of a calibration phantom according to FIG. 2.
Figure 4:
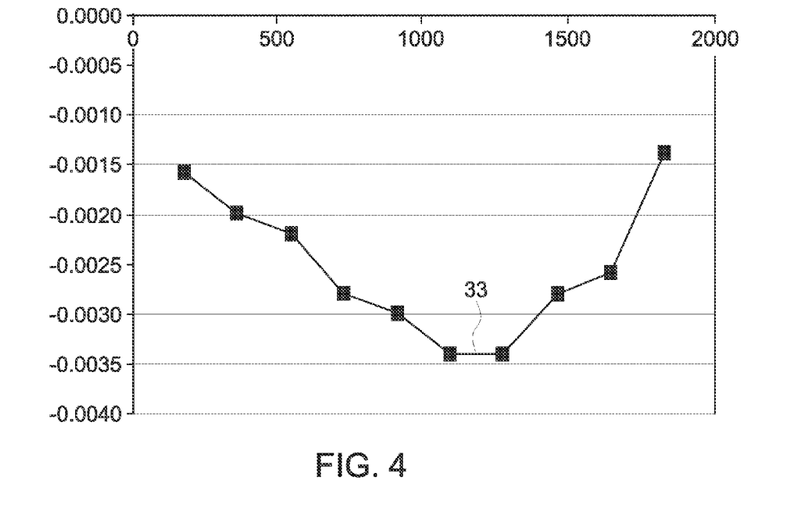
FIG. 4 an illustration of the diameter variation of the spheres of the calibration phantom over the detector extension.

In Column 3, Line 24, delete "FIG. 3 a" and insert -- FIG. 3 is a --, therefor.

In Column 3, Line 26, delete "FIG. 4 an" and insert -- FIG. 4 is an --, therefor.

Figure 5:
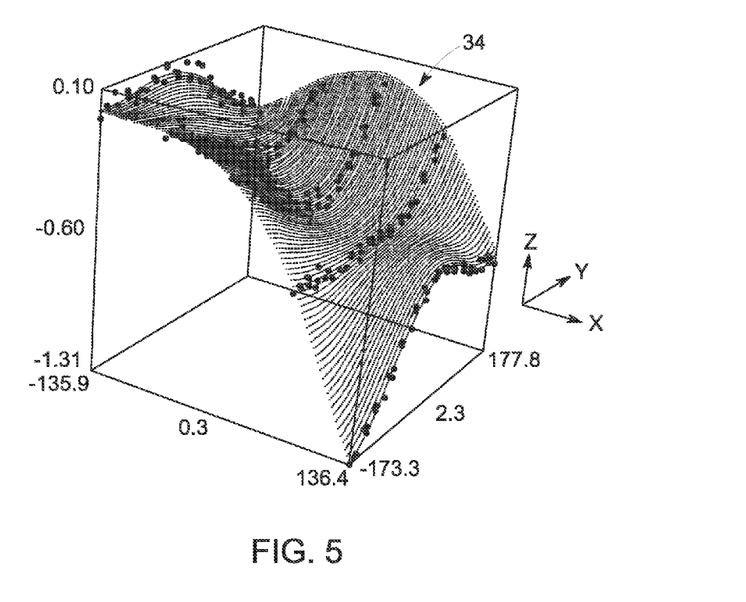
FIG. 5 a two-dimensional illustration of the diameter variation of the spheres of the calibration phantom over both detector extensions.

In Column 3, Line 29, delete "FIG. 5 a" and insert -- FIG. 5 is a --, therefor.

In Column 3, Line 32, delete "FIG. 6 a" and insert -- FIG. 6 is a --, therefor.

In Column 3, Line 34, delete "FIG. 7 a" and insert -- FIG. 7 is a --, therefor.

Figure 8:
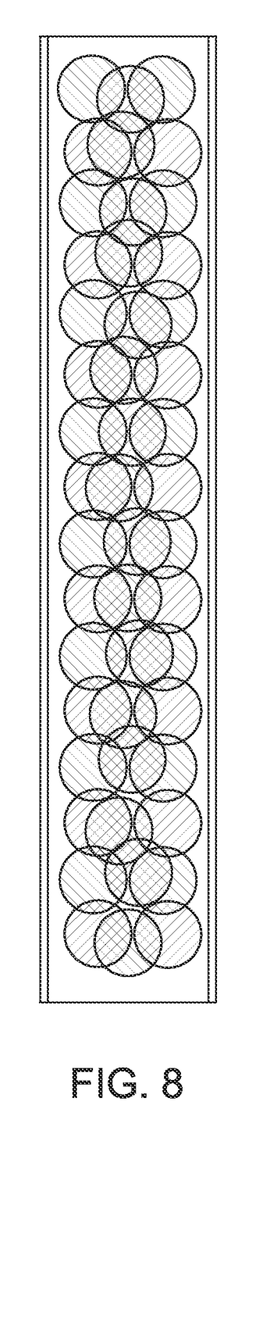
FIG. 8 a schematic reproduction of an x-ray image of a calibration phantom according to FIG. 6.

In Column 3, Line 36, delete "FIG. 8 a" and insert -- FIG. 8 is a --, therefor.

In Column 3, Line 38, delete "FIG. 9 a" and insert -- FIG. 9 is a --, therefor.

In Column 3, Line 40, delete "FIG. 10 a" and insert -- FIG. 10 is a --, therefor.

Signed and Sealed this
Twenty-second Day of March, 2016

Michelle K. Lee
*Director of the United States Patent and Trademark Office*

CERTIFICATE OF CORRECTION (continued)
U.S. Pat. No. 9,146,327 B2

IN THE CLAIMS

In Column 7, Line 9, in Claim 6, delete "at least on" and insert -- at least one --, therefor.

In Column 7, Line 14, in Claim 7, delete "at least on" and insert -- at least one --, therefor.